US008983571B2

(12) United States Patent
Davis et al.

(10) Patent No.: US 8,983,571 B2
(45) Date of Patent: Mar. 17, 2015

(54) METHOD FOR MEASURING LIVER FAT MASS USING DUAL-ENERGY X-RAY ABSORPTIOMETRY

(71) Applicant: General Electric Company, Schenectady, NY (US)

(72) Inventors: Cynthia Elizabeth Landberg Davis, Niskayuna, NY (US); Xin Wang, Clifton Park, NY (US); Tzu-Jen Kao, Watervliet, NY (US); Megan Pearl Rothney, Madison, WI (US)

(73) Assignee: General Electric Company, Niskayuna, NY (US)

( * ) Notice: Subject to any disclaimer, the term of this patent is extended or adjusted under 35 U.S.C. 154(b) by 176 days.

(21) Appl. No.: 13/915,876

(22) Filed: Jun. 12, 2013

(65) Prior Publication Data

US 2014/0371570 A1   Dec. 18, 2014

(51) Int. Cl.
 *A61B 5/00* (2006.01)
 *A61B 6/00* (2006.01)

(52) U.S. Cl.
 CPC ............... *A61B 5/4244* (2013.01); *A61B 6/50* (2013.01); *A61B 6/482* (2013.01); *A61B 5/4872* (2013.01); *A61B 6/469* (2013.01); *A61B 6/5217* (2013.01)
 USPC ....................................................... 600/407

(58) Field of Classification Search
 CPC .... A61B 5/4244; A61B 5/4872; A61B 5/469; A61B 5/482; A61B 5/50; A61B 5/5217
 See application file for complete search history.

(56) References Cited

U.S. PATENT DOCUMENTS

| 8,300,911 | B1 | 10/2012 | Payne et al. |
| 2004/0101086 | A1 | 5/2004 | Sabol et al. |
| 2006/0074288 | A1 | 4/2006 | Kelly et al. |
| 2006/0088198 | A1 | 4/2006 | Arnold |
| 2008/0071186 | A1 | 3/2008 | Kasahara |
| 2011/0235886 | A1 | 9/2011 | Kelly et al. |
| 2011/0280840 | A1 | 11/2011 | Blaser et al. |

OTHER PUBLICATIONS

Mendler et al., "Dual-Energy CT in the Diagnosis and Quantification of Fatty Liver: Limited Clinical Value in Comparison to Ultrasound Scan and Single-Energy CT, With Special Reference to Iron Overload", Journal of Hepatology, vol. 28, Issue 5, pp. 785-794, May 1998.
Hu et al., "Quantification of Absolute Fat Mass by Magnetic Resonance Imaging: a Validation Study Against Chemical Analysis", International Journal of Body Composition Research, vol. 9, Issue 3, pp. 111-122, 2011.
Fischer et al., "Quantification of Liver Fat in the Presence of Iron and Iodine: An Ex-Vivo Dual-Energy CT Study", Investigative Radiology, vol. 46, Issue 6, pp. 351-358, Jun. 2011.
Davidson et al., "Protocol for Measurement of Liver Fat by Computed Tomography", J. Appl. Physi0l, vol. 100, pp. 864-868, 2006.

*Primary Examiner* — Michael Rozanski
(74) *Attorney, Agent, or Firm* — Eileen B. Gallagher

(57) ABSTRACT

Methods for measuring liver fat mass are provided. One method includes acquiring dual-energy two-dimensional (2D) scan information from a dual-energy X-ray scan of a body and generating a dual-energy X-ray image of the body using the 2D scan information. The method further includes identifying a region of interest using the dual-energy X-ray image and determining a subcutaneous fat mass for each of a plurality of sections of the region of interest. The method also includes determining a liver fat mass for the region of interest based on the determined subcutaneous fat mass for each of the plurality of sections.

14 Claims, 6 Drawing Sheets

METHOD FOR MEASURING LIVER FAT MASS USING DUAL-ENERGY X-RAY ABSORPTIOMETRY

BACKGROUND OF THE INVENTION

This disclosure relates generally to medical diagnostic imaging methods and systems, and more particularly to medical diagnostic imaging methods and systems that acquire and process tissue information for measuring the liver fat levels of an individual.

Non-alcoholic fatty liver disease (NAFLD) has become a common form of liver disease. It occurs when fat is accumulated in liver without significant alcohol consumption. It is associated with insulin resistance, cardiovascular disease, and metabolic syndrome, such as obesity, combined hyperlipidemia, diabetes mellitus (type II), and high blood pressure. The prevalence of NAFLD in the United States is estimated to be between 10% and 33%. Accumulation of fat in liver can lead to steatohepatitis and cirrhosis, and thus liver fat level may be used as a parameter to quantify the severity of NAFLD. Liver biopsy is considered the gold standard for liver fat diagnosis. But it is costly, invasive, and may be subject to sampling error. The non-invasive imaging modalities for liver fat quantification include MRI (magnetic resonance imagining), proton magnetic spectroscopy ($^1$H MRS or simply MRS), ultrasound and CT scan (computed tomography scan). MRS has been considered the gold standard for in vivo quantification of liver fat. It allows the detection of low level liver fat. However, it is not widely available and requires long examination time.

Fat is more echogenic in ultrasound imaging, and thus liver with a higher fat level is brighter in the image. The sensitivity of ultrasound for liver fat quantification is acceptable, but its capability in grading the degree of liver fat level is limited. Furthermore, ultrasound is unable to distinguish brightness in liver caused by high liver fat level and by high fibrous level. CT has also been studied to estimate liver fat level. In CT imaging, low attenuation indicates low tissue density. Therefore, lower mean liver attenuation in the CT image indicates a higher liver fat level. However, there is risk in CT imaging due to high dose of ionizing radiation in CT imaging and these examinations cannot be conducted frequently. Furthermore, CT imaging is costly. 2D dual energy X-ray absorptiometry has the capability to distinguish the difference between fat and fibrous tissues better than ultrasound, but with a significantly lower x-ray dose and cost than CT imaging. However, due to the 2-D nature of the imaging it is difficult to distinguish between subcutaneous fat, visceral fat and fat in the liver.

Therefore, there is a need for a method and system to accurately measure liver fat levels that can be conducted frequently during routine exams. More specifically, there is a need for a 2-D dual energy x-ray absorptiometry method and system to more accurately measure liver fat by measuring and correcting for subcutaneous fat and other visceral fat.

BRIEF DESCRIPTION OF THE INVENTION

In accordance with an aspect of this invention, a method to quantify liver fat from 2-D dual-energy X-ray absorptiometry is disclosed. The method comprises generating at least one dual-energy X-ray skeletal image of the body and at least one soft tissue image of a body using a material decomposition method; identifying a region of interest corresponding to a liver (liver ROI); determining a soft tissue composition profile for the liver ROI which includes total fat mass; identifying a body region of interest (body ROI) wherein the body ROI corresponds to a region extending from the liver ROI to the sides of the body; determining a soft tissue composition profile of the body; estimating subcutaneous fat of the body ROI using the soft tissue composition profile; determining estimates of subcutaneous fat of the liver ROI from the subcutaneous fat of the body ROI; and determining a liver fat mass for the liver based on subtraction of the subcutaneous fat of the liver ROI from the total fat mass of the liver ROI.

In accordance with an aspect of the disclosure, a method is also disclosed which includes determining a liver fat mass for the region of interest based on the determined subcutaneous fat mass for a plurality of liver sections.

Various other features, aspects, and advantages will be made apparent to those skilled in the art from the accompanying drawings and detailed description thereof.

DETAILED DESCRIPTION OF THE INVENTION

Figure 1:
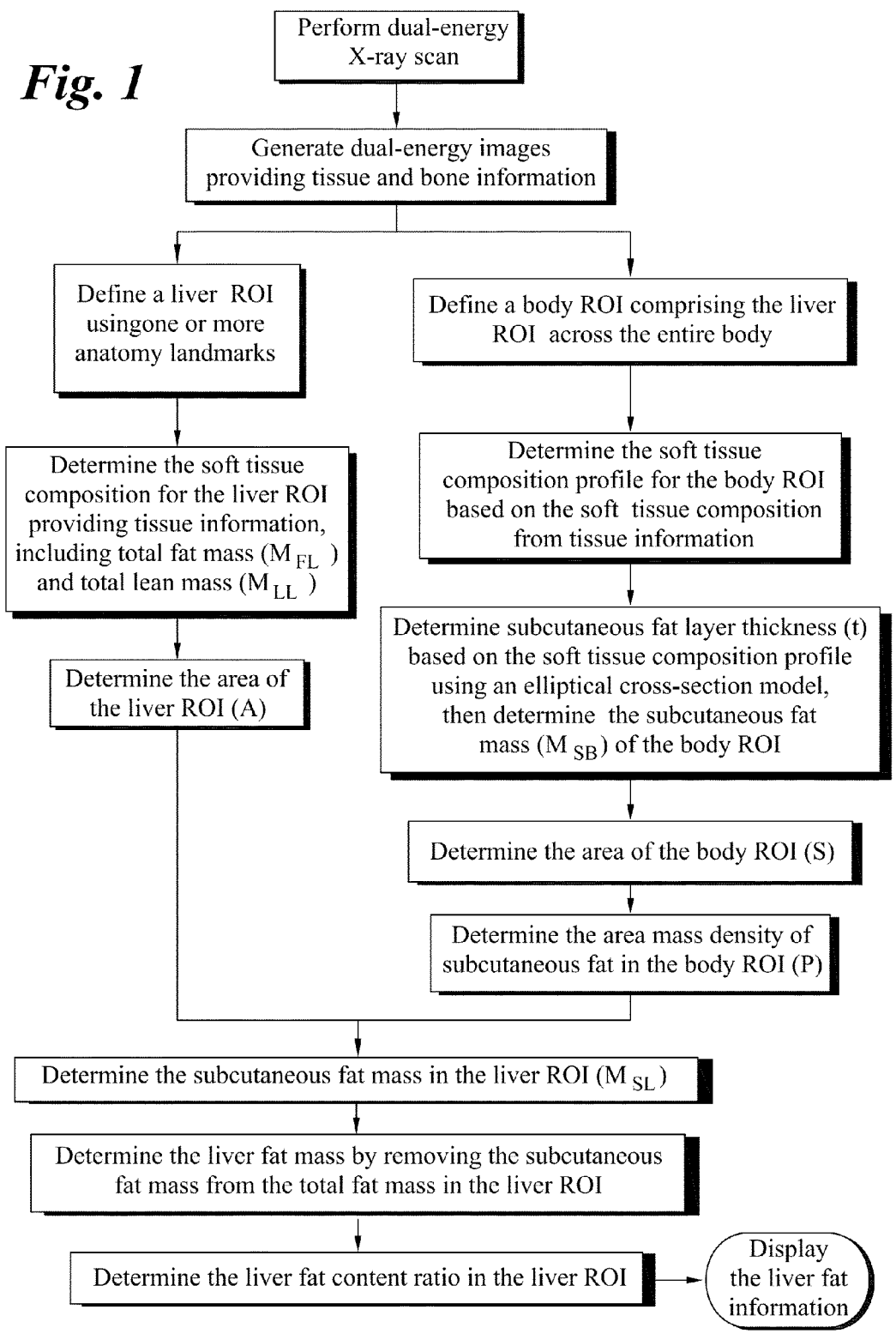
FIG. 1 is a flow diagram of an exemplary embodiment of a method for calculating the liver fat mass of a subject.

Exemplary embodiments of dual-energy X-ray imaging methods and systems for scanning bodies to obtain estimate liver fat mass in a subject using dual-energy X-ray absorptiometry (DXA) is described below.

In general, in certain embodiments, the method involves acquiring a dual-energy x-ray 2-D scan of a subject's liver area and a portion of the subject's body around and including the liver area, and then generating a tissue image from the raw data with material decomposition method. As such the method includes acquiring liver and body composition information using the dual energy scan and segmenting the tissue type. Segmenting the tissue from the body area provides an approximation of the subcutaneous fat that is present in the body as well as around the subject's liver. This amount of subcutaneous fat can be subtracted from the total fat composition of the liver to provide a measure of fat present in the liver itself. As such, the method provides a more accurate and convenient measure of liver fat by measuring and correcting for subcutaneous fat in the radiographic attenuation image of the liver.

More specifically, during the dual-energy x-ray scan an image of a portion of or the entire patient may be acquired, which includes tissue information, from which soft tissue composition may be determined, and skeletal information relating to the bones in the skeleton. For example, a dual-energy detector receives a beam after the beam has passed through the subject and generates electrical signals indicating the attenuation of the beam by the subject within distinct first and second energy ranges. Images such as a bone density images, tissue images, particularly soft tissue images, or a combination thereof are produced based on the attenuation of the x-ray radiation in the first and second energy ranges. Thus, the dual-energy system allows not only the formation of a radiographic attenuation image, but also the mathematical analysis of the composition of the attenuating material by dual-energy techniques. As such, dual-energy techniques may be used that quantitatively compare the attenuation of radiation at two energies to distinguish between bone and soft tissue, as well as to distinguish between different types of tissue, thus allowing for the identification of different types of soft tissues for example fat tissue and lean tissue.

Generally a soft tissue composition profile may be generated from identifying the soft tissue in the scan region and measuring soft tissue thickness or mass across one or more lines of the scanned body: for example, one or more scan lines within the body ROI. The soft tissue composition profile is generally higher at the borders or outer region of the body identified by the scan lines compared to the profile in the center region of the scan lines which represent the middle of the body. The soft tissue composition profile shows the change in thickness or masses of the soft tissue based on, for example, the change in attenuation of an x-ray signal through that portion of the body. It should be noted that the values for the soft tissue composition profile may be an average composition over the vertically integrated scan lines for all horizontal positions. Accordingly, the soft tissue composition profile is a composition distribution in the horizontal direction, namely from right to left or left to right across the entire body ROI. In some embodiments, the soft tissue composition profile may be generated only for one section of the body ROI or limited area.

The subcutaneous fat mass or area may then be determined based on the soft tissue composition profile whereby the ends or boundaries of the subcutaneous fat layer are represented by two individual peaks. As previously stated, the peaks occur, as the subcutaneous fat layer may be more pronounced at the outer edges of the body ROI. The subcutaneous fat layer thickness is then measured by thresholding the soft tissue composition profile. For example, for each side of the body ROI, the peak is specifically identified. The minimum of the profile may then be determined. The threshold may be set at a predetermined value from the minimum to the maximum (peak); for example at the point of maximum derivative.

Accordingly, the initial calculated thickness of the subcutaneous fat mass or area is the distance from the threshold to the end of the profile, which is then multiplied by an empirically derived constant. The constant may be derived based on empirical studies or simulations. It should be noted that in various embodiments the subcutaneous fat mass or area may be determined differently or by using different methods and that value applied.

As such, in certain embodiments, using the soft tissue information from the dual-energy X-ray scan, or the soft tissue composition profile, a tissue thickness along one or more scan lines may be determined. The peak tissue thickness defines a distance across the imaged body, for example, from an anterior region to a posterior region of the body, which is used as the length of the minor axis of the ellipse. Furthermore, the width of the DXA image at a middle or average portion of the image defines the length of the major axis. Using a pixel measuring method, the width may be determined as the distance from one side of the imaged body to the other side using a pixel count (as each pixel in the full body dual-energy X-ray image has a known size in the vertical and horizontal direction). The pixel count may start, for example, from a left edge (i.e., air/tissue boundary) of the imaged body and continue to a right edge (i.e., air/tissue boundary) of the imaged body.

Figure 2:
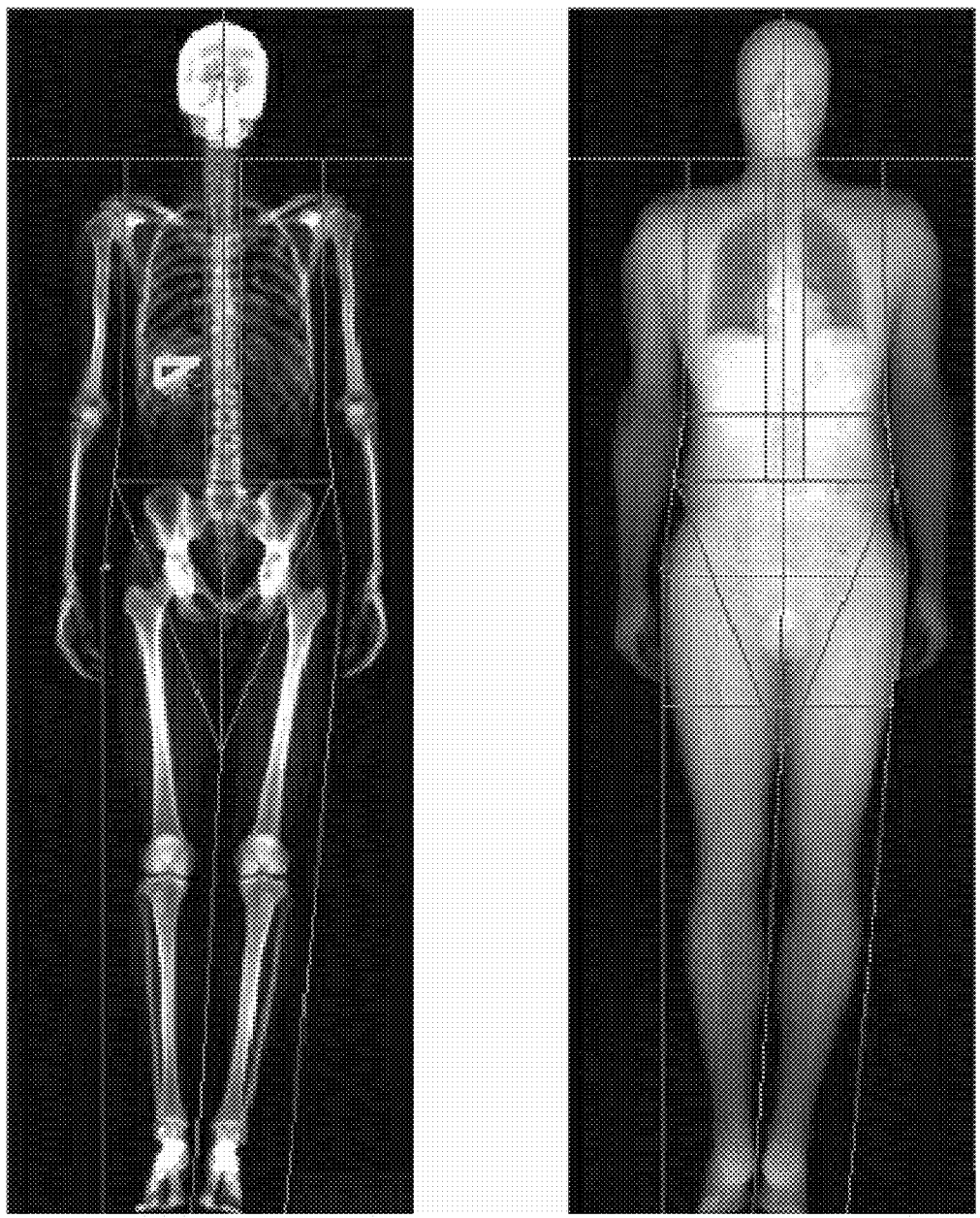
FIG. 2 is a diagram of an exemplary embodiment of a dual-energy X-ray bone and soft tissue composition identifying a liver ROI.

FIG. 1 is a flow diagram of an exemplary embodiment of a method for calculating the liver fat mass of a subject. After generating the dual energy images, in a first step, a region of interest corresponding to liver (liver ROI) on the 2-D dual-energy X-ray image is identified. This is shown in FIG. 2 which shows a dual-energy X-ray image identifying a liver ROI of a subject from the bone and soft tissue composition. The area may have an arbitrary shape such as a rectangular region or a quadrant that approximates the liver area and provides a measurement of area (A). Using soft tissue decomposition, total fat mass of the liver ($M_{FL}$) and total lean mass of the liver ($M_{LL}$) may be determined.

Figure 3:
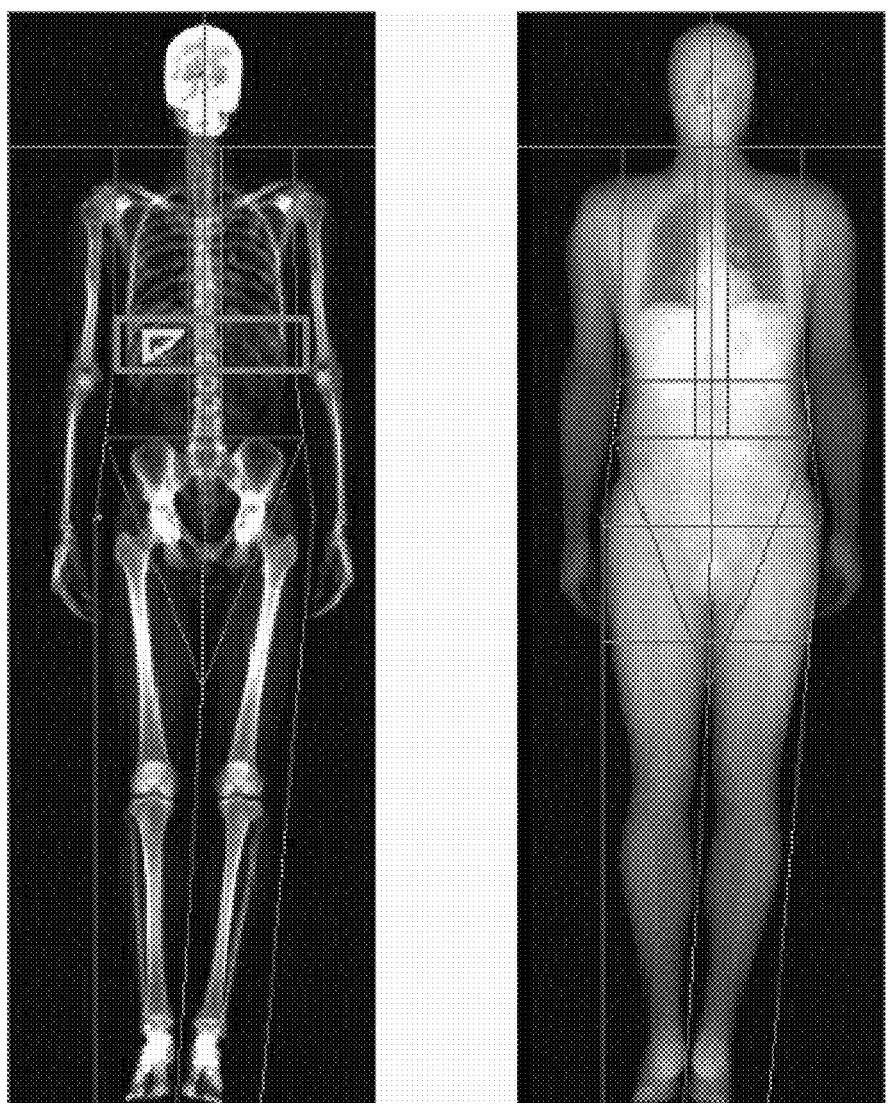
FIG. 3 is a diagram of an exemplary embodiment of a dual-energy X-ray skeletal and soft tissue composition identifying the body ROI.

Using the liver ROI, a second region of interest, which extends from the liver ROI horizontally, all the way to the side of the body (body ROI), is also defined. This is shown in FIG. 3 which is a dual-energy X-ray image showing the skeletal (bone) and soft tissue composition. The area may be demarcated using the same vertical dimensions as the liver ROI. From this second region of interest, by soft tissue decomposition and assuming an elliptical cross-section of the subcutaneous fat, the fat layer thickness (t) and mass of subcutaneous fat (MSB) in the body ROI may be determined.

Figure 4:
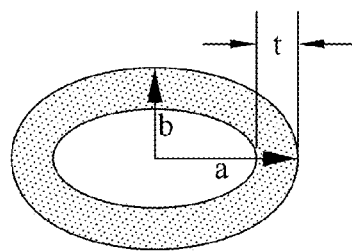
FIG. 4 illustrates an exemplary embodiment of a diagram illustrating the use of an elliptical model to approximate the cross-section of an imaged section of a body ROI.

FIG. 4 illustrates an exemplary embodiment of a diagram illustrating the use of an elliptical model to approximate the cross-section of an imaged section of a body ROI. It should be noted that any method known in the art may be used to calculate the perimeter or circumference of the ellipse. As shown in FIG. 4, the height (semi-minor axis (b)) of the ellipse of the elliptical model is determined from a peak tissue thickness at the body ROI, and width (semi-major axis (a)) of the ellipse is determined from a width of the dual x-ray image at the body ROI.

The soft tissue composition profile can be determined as an average composition over the vertically integrated scan lines for all the horizontal positions over the entire body ROI. The subcutaneous fat layer thickness (t) (FIG. 4) can be then determined by thresholding the soft tissue composition profile.

From the image, the area of the body ROI may be calculated (S) and as such the area mass density of the subcutaneous fat (P) of the body may also be determined wherein:

$$P = M_{SB}/S$$

The mass density is then used to compute the subcutaneous fat mass in the liver ROI ($M_{SL}$) by assuming that the percentage of subcutaneous fat in the tissue is uniform around the liver area. As the subcutaneous fat mass in the liver ROI is determined by multiplying the liver area by P:

$$M_{SL} = P*A$$

The fat mass in the liver may then be determined by subtracting the subcutaneous fat mass from the total fat mass in the liver ROI:

$$M = M_{FL} - M_{SL}$$

The results may also be displayed or represented as a liver fat content ratio in the liver ROI wherein:

$$\text{—\% LiverFat} = M/(M_{FL}+M_{LL}) \times 100\%$$

As such, it should be noted that the liver fat content may be displayed in numerous ways wherein the data may be processed, stored, or displayed in real-time during a scanning session as the data is received, or the data stored for off-line processing or long-term data monitoring. Similar methods of data storage and display are described in more detail in U.S. Pat. No. 8,300,911 entitled "Methods and Apparatus for Measuring Visceral Fat Mass" issued Oct. 30, 2012 and incorporated in its entirety herein by reference. In certain embodiments, the liver fat content may be displayed in numerous ways, including but not limited to percent fat in the liver, fat mass of the liver, a fat ratio, a fat score wherein the value obtained is compared to other subjects of similar height and age and a score would reflect a likelihood of NAFLD or fibrotic liver disease or combinations thereof.

In certain embodiments, the liver fat content may be combined with other measurements, qualitative or quantitative of wellness or health. For example as one variable in a health assessment which may include % body fat, bone density, liver fat mass, visceral fat, BMI and any other measurements made on the DXA; for example included with an assessment of myocardial or epi-cardial fat. The assessment may be an indicator of risk of metabolic syndrome or diabetes.

Figure 5:
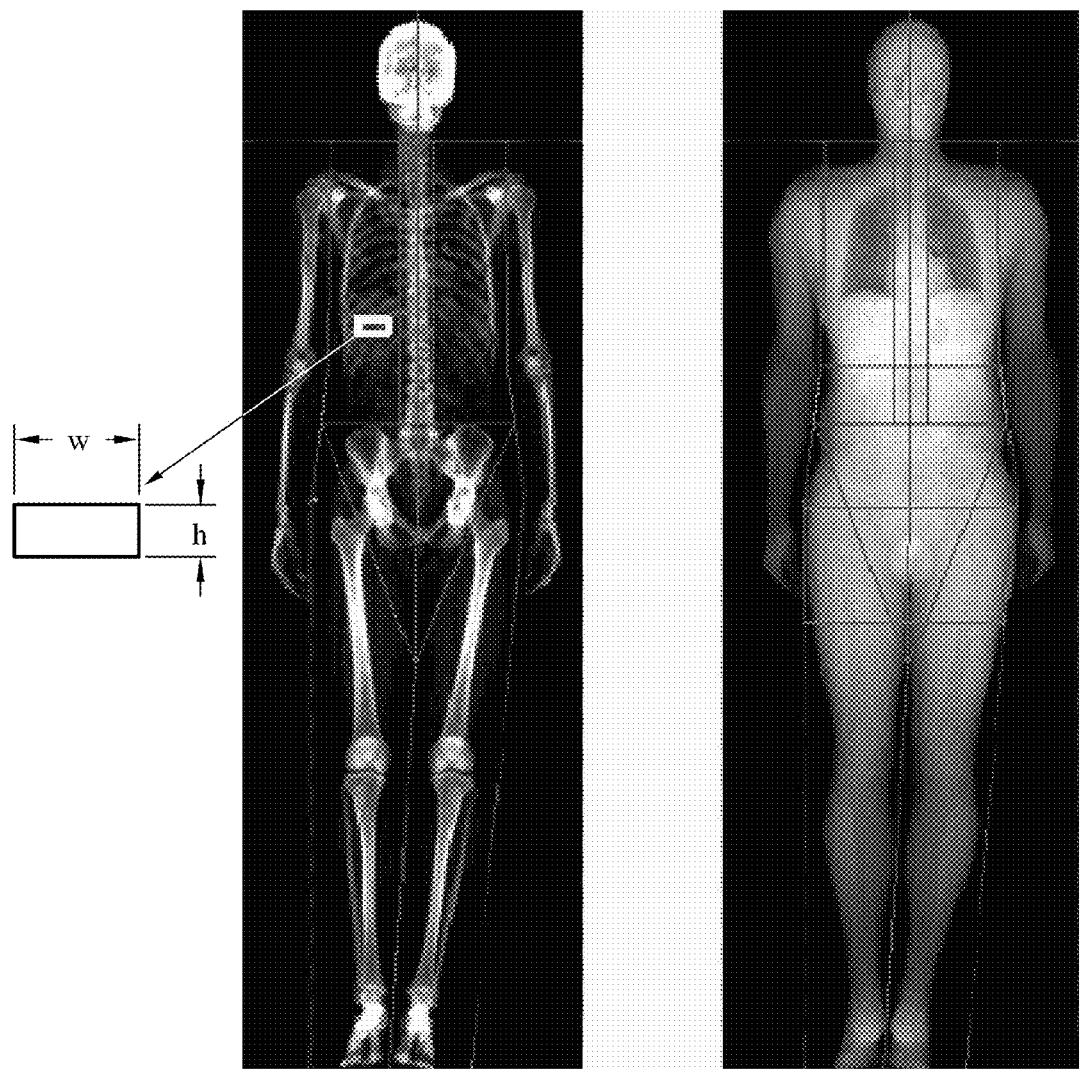
FIG. 5 is a diagram of an exemplary embodiment of a dual-energy X-ray where the liver ROI is defined as a rectangular area.
Figure 6:
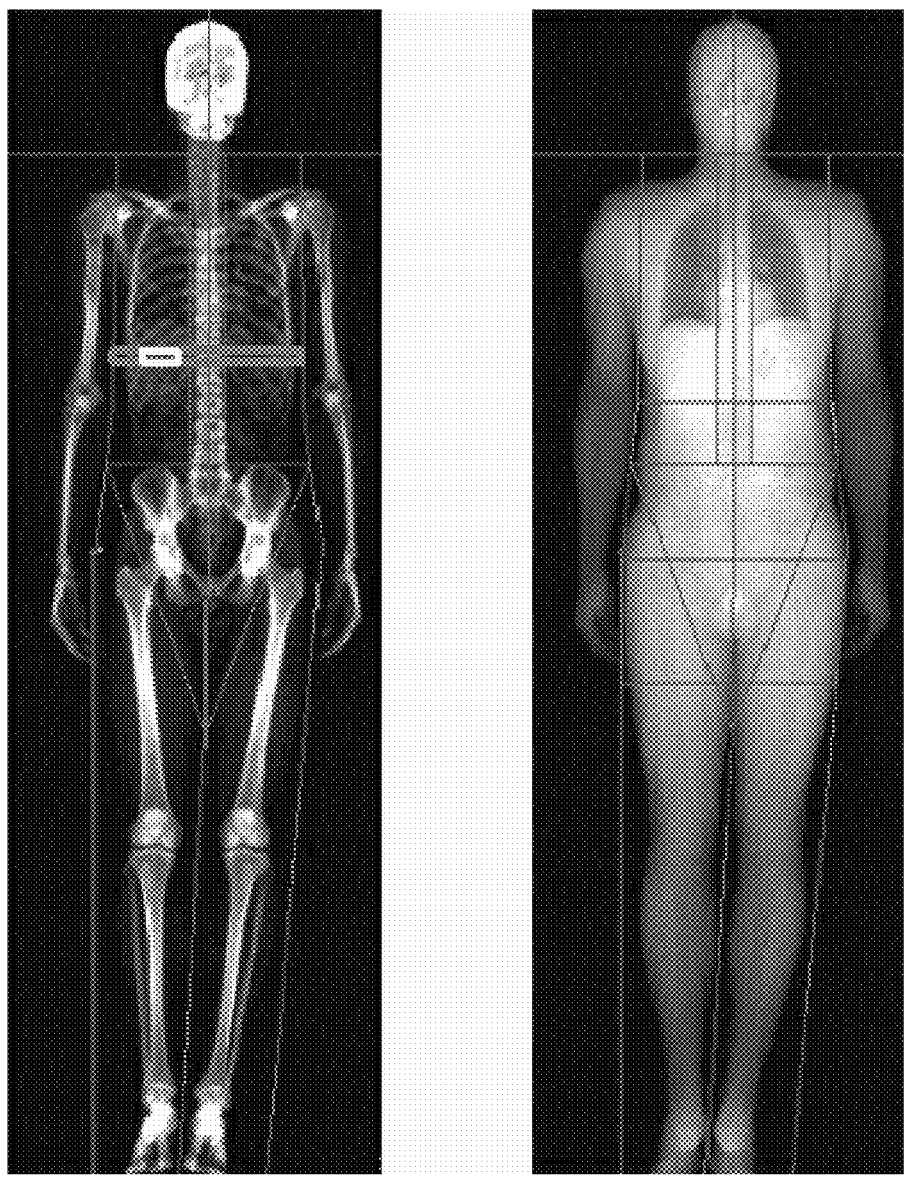
FIG. 6 is the corresponding body ROI from FIG. 5 which incorporates the liver ROI.

In other embodiments the liver ROI may be defined as a rectangular area, with horizontal with horizontal dimension of W, and vertical dimension of H. This is illustrated in FIG. 5. The corresponding body ROI, which also incorporates the liver ROI, may be defined on the same level and with the same vertical dimensions as the liver ROI, with the area extending across the subject. This is shown in FIG. 6.

The tissue composition profile for the body ROI may be determined based on soft tissue composition from the dual-energy X-ray scan. The subcutaneous fat layer thickness (t) is based on the soft tissue composition profile by using an elliptical cross-section mode.

Figure 7:
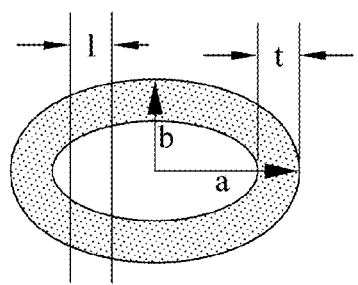
FIG. 7 is elliptical model defining values of the axis (a and b) as well as fat layer thickness (t) and the length of the ellipse (l) covered by the liver.

As shown with reference to the elliptical model in FIG. 7, the height (semi-minor axis (b)) of the ellipse of the elliptical model is determined from a peak tissue thickness at the body ROI, and width (semi-major axis (a)) of the ellipse is determined from a width of the dual x-ray image at the body ROI.

The soft tissue composition profile is determined as an average composition over the vertically integrated scan lines for all the horizontal positions over the entire body ROI. The subcutaneous fat layer thickness can be then determined by thresholding the soft tissue composition profile.

As such, the perimeter of the ellipse of the elliptical model (denoted by C), is calculated as:

$$C = 4aE(e)$$

where a is the semi-major axis, e is the eccentricity, and the function E is the complete elliptical integral of the second kind.

In certain embodiments, the perimeter (C) can also be approximated as:

$$C = 2\pi \sqrt{\frac{a^2 + b^2}{2}}$$

wherein a and b are the axis as shown in FIG. 7.

The mass density (D) of the subcutaneous fat layer in the body ROI along the length of the ellipse is then calculated:

$$D = M_{SB}/C$$

wherein MSB is the mass of subcutaneous fat in the body ROI.

The length of the ellipse covered by the liver ROI (L) is:

$$L = 2l$$

calculated from the arc length (l) as shown in FIG. 7 calculated from the measurement of the axis a and b and w (width of the liver ROI) and can be approximated by the width of the liver ROI. The subcutaneous fat mass in the liver ROI ($M_{SL}$) is then L*D.

The liver fat mass (M) may then be determined as previously described by subtracting the subcutaneous fat mass from the total fat mass in the liver ROI.

A region of interest for the spleen may also be defined below the left lobe of the liver. The spleen is not prone to fat accumulation and the tissue density is similar to that of the liver fibrous tissues. Any fat tissue found in this region of interest once the subcutaneous fat has been removed can be attributed to visceral fat (Mv) or intramuscular fat. This additional fat may be removed from the total liver fat (M) wherein:

$$M = M_{FL} - M_{SL} - M_V$$

In certain instances it is understood the cross-section of the may not necessarily have a smooth, consistent and/or regular cross-section and other approximations may be used in place of an elliptical model.

In accordance with various embodiments, using the soft tissue information from the dual-energy X-ray scan, or the soft tissue composition profile, a tissue thickness along one or more scan lines may be determined. The peak tissue thickness defines a distance across the imaged body, for example, from an anterior region to a posterior region of the body, which is used as the length of the minor axis of the ellipse. Furthermore, the width of the DXA image at a middle or average portion of the image defines the length of the major axis. Using a pixel measuring method, the width may be determined as the distance from one side of the imaged body to the other side using a pixel count (as each pixel in the full body dual-energy X-ray image has a known size in the vertical and horizontal direction). The pixel count may start, for example, from a left edge (i.e., air/tissue boundary) of the imaged body and continue to a right edge (i.e., air/tissue boundary) of the imaged body.

It should be noted that a full body or total body scan of the entire body may be performed as a single scanning operation, which may be a low dose mode scan. However, instead of a full body or total body scan, individual smaller scans of a body region of interest, for example may be performed in single sweep or rectilinear scans.

In certain embodiments, the identification of a liver ROI may be performed in different ways. For example, the liver region may be determined manually by an operator viewing a full body dual-energy X-ray image and placing a line (e.g., using a mouse) at the region of the image where the liver is observed. It should be noted that the line may be defined by two endpoints or may be generated and then increased or decreased in length as needed, as well as moved or adjusted. The liver ROI may be identified automatically using any method, for example, a template matching method or by searching for a specific bone or structure in an adjacent region.

For example, in certain embodiments the liver ROI is identified being right of the median plan of the body (the spine) and may be located based on rib locations (ribs 9 to 11) in the skeletal image using standard image processing algorithms such as thresholding and filtering. In other embodiments, the liver location based on the diaphragm which is clearly visible in a DXA image can be used as well. If breath hold techniques described below are used the liver should be in a reliable location with respect to the diaphragm. The breath can be held during a scan such that the diaphragm is pressed down the liver extends from under the rib cage and the diaphragm can be identified. While in other cases the liver ROI may be identified at a set distance from the top of the iliac crest. The visceral fat region was define as a ratio from the top of the iliac crest to the total height to find the 3/4th lumbar which is measured based upon the DXA bone measurements. For the liver the desired location would be at the lower part of the liver which is on the average person is at a level between the first and third lumbar vertebra. In still others, the liver ROI may simply be identified from the image itself.

It should be noted that when the automatic identification method is used, an operator may still adjust the identified location of the land mark, for example, by moving an automatically generated line. Therefore, it should be noted that any method may be used to determine landmark and the identification thereof is not limited to the methods described above.

In certain embodiments, the liver ROI may be defined as a portion of the liver; for example, including but not limited to, a right lobe and left lobes or right and left hemiliver, left lateral, left medial, right lateral, right medial, quadrate, caudate, papillary, or combinations thereof. As such, the fat content of the liver may be based on a portion of the liver and the fat content identified for that portion or a plurality of sections.

Referring again to FIGS. 2, 3, 5, and 6, the figures illustrate a dual-energy X-ray image. The images are generated from a full body scan, which in some embodiments includes acquiring all bone and tissue information during a single scan, for example, a single imaging pass or operation. The total body scan may be acquired using different dual-energy X-ray imaging systems, for example, the Lunar iDXA® imaging system available from GE Healthcare (Wauwatosa, Wis.) or other bone densitometry systems. The Lunar iDXA imaging system generally has no parallax in the transverse scanning direction. An embodiment of a dual-energy X-ray imaging system is described in more detail in aforementioned U.S. Pat. No. 8,300,911.

During operation, two X-ray beams having different energy levels are utilized to scan a subject, for example, to scan a body of a human patient (e.g., a patient) to image the body of the subject. The acquired image(s), including tissue and bone information from the imaged body, particularly determined tissue composition (body composition) and tissue thickness information, is used to calculate a liver fat mass of the liver ROI region of the subject. The image(s) may be generated in part from determined tissue information and acquired during a dual-energy X-ray scan.

In certain embodiments, it may be desirable to position the body to improve the visualization of the liver ROI. For example, it may be desirable to acquire the image when the subject is performing a breath hold, as exhaling pushes the diaphragm and therefore the liver down. In other embodiments, it is desirable to ensure that breast tissue is not positioned on top of the liver ROI. In other embodiments, it is desirable to ensure that the arm tissue is not touching the body.

It also should be noted that different methods or models may be used to determine the liver fat mass in different sections of the liver of the 2D planar image(s) from the dual-energy X-ray imaging system. It further should be noted that although the various embodiments are described in connection with a dual-energy X-ray imaging system, the various embodiments are not limited to a dual-energy X-ray imaging system or a particular configuration thereof.

During operation, the dual-energy X-ray imaging system may be configured to operate in either a dual-energy X-ray mode or a single energy X-ray mode. In the single energy X-ray mode, the X-ray source emits X-rays in a narrow band of energies of a few keV and in the diagnostic imaging range of approximately 20-150 keV. In the dual-energy X-ray mode, the X-ray source emits radiation in two or more bands of energy emitted simultaneously or in rapid succession. The X-ray source may also be configured to emit a single broadband of energy of more than a few keV over the diagnostic imaging range. The dual-energy X-ray imaging system may be switched between the dual-energy X-ray mode and the single energy X-ray mode by increasing or decreasing the X-ray source voltage and/or current. The dual-energy X-ray imaging system may also be switched between the dual-energy X-ray mode and the single energy X-ray mode by removing or adding a K-edge filter. It should be noted that the X-ray source may emit X-rays at different energies or ranges of energies.

The dual-energy X-ray mode allows the acquisition of both tissue information and skeletal (bone) information, for example, soft tissue information, such as fat density or fat thickness information. Accordingly, the dual-energy X-ray mode allows for both soft tissue and skeletal imaging of the subject using attenuation information from different energy levels. It should be noted that in the single energy X-ray mode, higher resolution images also may be generated.

EXPERIMENTAL

A preliminary study was performed with 32 obese subjects comparing CT and iDXA liver fat measurements. DXA and CT images were acquired of the region from above the iliac crest to the top of the diaphragm. The CT measurement is used as the reference for this study. The gold standard measurement of a liver punch biopsy was not available for these subjects. The CT measurement is based upon manual identification and segmentation of the liver and spleen. A ratio of the Hounsfield Units (HU) value for ROI's corresponding to the liver and spleen is taken. A ratio of spleen to liver of greater than 1 is indicative of high fat content or significant hepatic steatosis. The CT gold standard calculation is described in more detail in "Protocol for measurement of liver fat by Computer tomography", Lance E. Davidson, Jennifer L. Kuk, Timothy S. Church, Robert Ross, J Appl Physiol 100: 864-868, 2006.

The DXA images were obtained and processed according to the preferred embodiment outlined above. A dual energy scan of the subjects was acquired and the fat, muscle and bone tissues were segmented. The liver ROI was manually segmented and the tissue composition of the ROI found. The DXA liver ROI fat composition was found with and without the subcutaneous fat removal as outlined above. Upon calculation of a percentage fat content in the liver the liver was graded on the standard biopsy analysis scale. For this scale a grade of 0 to 4 for liver fat content is assigned a shown on the graphs of FIGS. 8 and 9 described below. Grade 0 represents no steatosis, Grade 1 is less than <10% liver fat content, Grade 2 is between 10% and 30%, Grade 3 is between 30% and <60%, and Grade 4 is greater than 60%. For a biopsy sample a liver fat level higher than 5% is of clinical significance.

Figure 8:
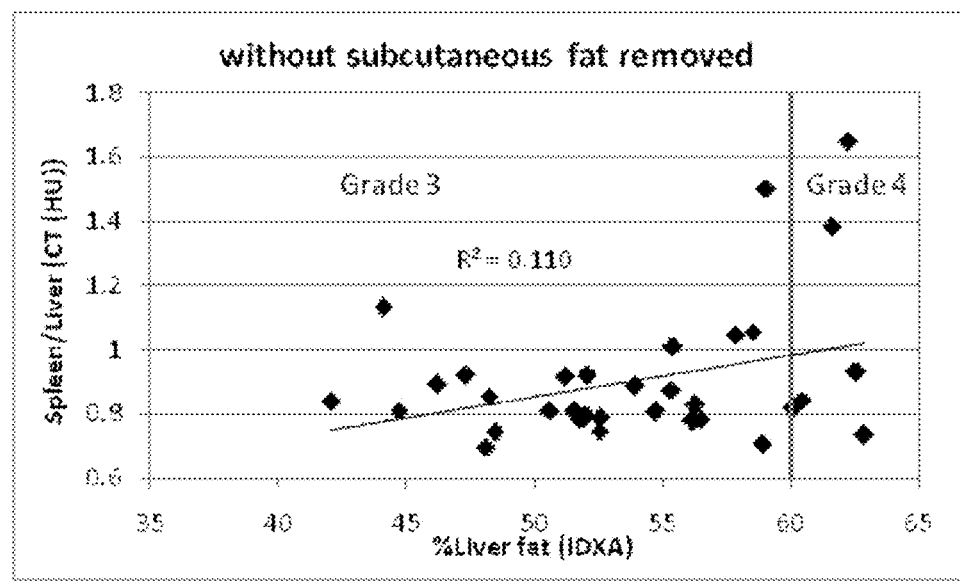
FIG. 8 is a graphical representation of patient data without subcutaneous fat removed from the calculation with a liner fit ($R^2$) to the standard and identified by grade.

FIG. 8 is a graphical representation of the obese subject data from the iDXA system without the subcutaneous fat removal. This data is compared directly to the spleen to liver ratio from the CT analysis. A linear fit ($R^2$) to the CT data is shown and the DXA identified fat content is graded.

Figure 9:
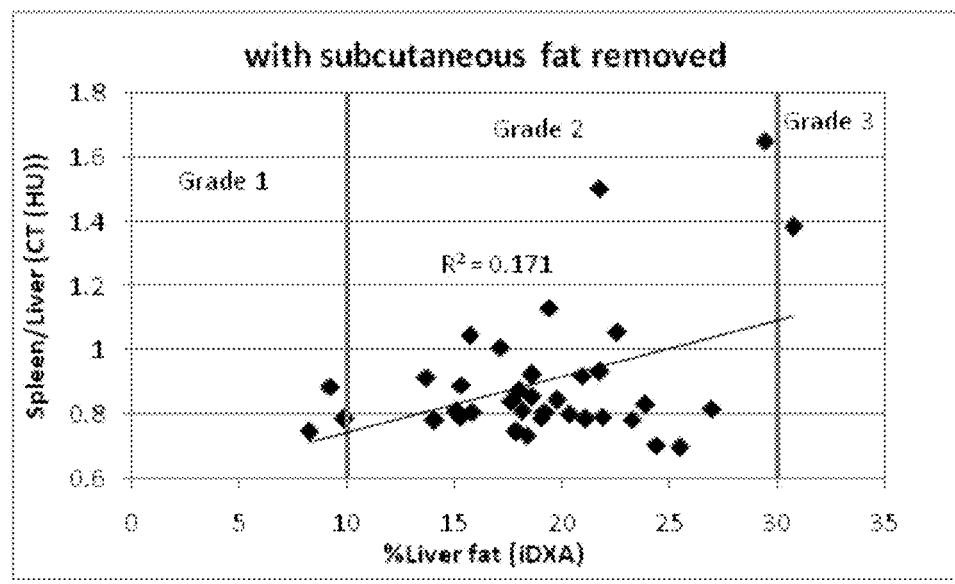
FIG. 9 is a graphical representation of patient data shown in FIG. 8 with subcutaneous fat removal.

FIG. 9 is a graphical representation of patient data shown in FIG. 8 with the subcutaneous fat removed from the DXA liver fat analysis using the techniques described above. The fat removal improves the $R^2$ of the linear fit of the DXA % fat to the CT measurement of spleen to liver HU ratio. One can conclude that there is an overestimation of the fat content of the liver in FIG. 8 for the DXA measurement due to the subcutaneous fat. In addition, the biopsy grading scale further compartmentalized into high medium or low fat content is shown. With this binning of the data and the subcutaneous fat removal the CT and iDXA measurements correlate well to give clinically actionable information. The CT measurement and DXA measurement with sufficient patient data can be better correlated with a calculated CT-HU and fat density empirical correction factor. In addition, the correction factors assumed in our model will need to be optimized to correlate to the true gold standard of liver fat biopsy scales.

While the disclosure has been described with reference to various embodiments, those skilled in the art will appreciate that certain substitutions, alterations and omissions may be made to the embodiments without departing from the spirit of the disclosure. Accordingly, the foregoing description is meant to be exemplary only, and should not limit the scope of the disclosure as set forth in the following claims.

What is claimed is:

1. A method for determining liver fat mass of a body, the method comprising:
    performing a dual-energy X-ray scan of a body;
    generating at least one dual-energy X-ray skeletal image of the body and at least one soft tissue image from the dual-energy X-ray scan of the body using a material decomposition method;
    identifying a region of interest corresponding to a liver (liver ROI) on the dual-energy X-ray scan;
    determining a soft tissue composition profile for the liver ROI wherein said composition profile includes total fat mass;
    identifying a body region of interest (body ROI) wherein the body ROI corresponds to a region extending from the liver ROI to the sides of the body;
    determining a soft tissue composition profile of the body ROI based on the soft tissue image from the dual-energy x-ray scan;
    estimating subcutaneous fat of the body ROI using the soft tissue composition profile of the body ROI;
    determining estimates of subcutaneous fat of the liver ROI from the subcutaneous fat of the body ROI; and
    determining a liver fat mass for the liver based on subtraction of the subcutaneous fat of the liver ROI from the total fat mass of the liver ROI.

2. The method of claim 1, wherein estimating of the subcutaneous fat of the body ROI comprising using an elliptical model.

3. The method of claim 2, wherein the major axis of the elliptical model is determined from a peak tissue thickness from a cross-section of the body ROI and the minor axis of the elliptical model is determined from a width of the dual-energy X-ray scan at the cross-section of the body ROI.

4. The method of claim 1, further comprising identifying the liver ROI using bone or diaphragm information from the dual-energy image X-ray skeletal from the dual-energy X-ray scan.

5. The method of claim 1 wherein the liver ROI comprises a section of the liver.

6. The method of claim 1 further comprising generating a soft tissue composition profile for a plurality of sections within the liver ROI for use in determining subcutaneous fat mass for each of the plurality of sections.

7. The method of claim 1 wherein the liver ROI is defined as a rectangular region.

8. The method of claim 7 wherein the body ROI is aligned with the vertical dimension of the liver ROI across the scanned body.

9. The method of claim 8 wherein estimating subcutaneous fat of the body ROI using the soft tissue composition comprises determining a mass density (D) value of a subcutaneous fat layer in the body using an elliptical model $$D = M_{SB}/C;$$

wherein $M_{SB}$ is a subcutaneous fat mass of the body ROI determined from a subcutaneous fat layer thickness (t) of the elliptical model; and
C is the perimeter of an ellipse calculated as $$C = 2\pi \sqrt{\frac{a^2 + b^2}{2}};$$

wherein
    b is the height of the semi-minor axis of the ellipse determined from a peak tissue thickness at the body ROI; and
    a is the width of the semi-major axis of the ellipse determined from a width of the dual x-scan image at the body ROI.

10. The method of claim 9 further comprising determining subcutaneous fat mass in the liver ($M_{SL}$) using the mass density value of the subcutaneous fat layer in the body (D) wherein $M_{SL}$=LD, such that L is defined as twice the arc length of the ellipse covered by the liver ROI.

11. The method of claim 10 wherein a region of interest corresponding to a spleen is identified and tissue density of the spleen is used to approximate liver fibrous tissues in the liver region of interest.

12. The method of claim 11 further comprising attributing any fat tissue found in the spleen region of interest to be visceral fat ($M_V$) and M, the liver fat mass may be calculated by:

$$M = M_{FL} - M_{SL} - M_V$$

$M_{FL}$=total fat mass of the liver;
$M_{SL}$=subcutaneous fat mass of the liver; and
$M_V$=visceral fat mass of the liver.

13. The method of claim 1 further comprising displaying liver fat information.

14. The method of claim 13 wherein liver fat information comprises percent fat in the liver, fat mass of the liver, a ratio of fat content, a fat score, or a combination thereof.

* * * * *